United States Patent [19]

Lloyd

[11] 4,411,996
[45] Oct. 25, 1983

[54] PROCESS FOR ISOMERIZING GLUCOSE

[75] Inventor: Norman E. Lloyd, Clinton, Iowa

[73] Assignee: Nabisco Brands, Inc., Parsippany, N.J.

[21] Appl. No.: 393,845

[22] Filed: Jun. 30, 1982

[51] Int. Cl.$^3$ ............................ C12P 19/24; C12N 9/96
[52] U.S. Cl. ........................................... 435/94; 435/188
[58] Field of Search ............................ 435/94, 234, 188

[56] References Cited

U.S. PATENT DOCUMENTS

| 3,826,714 | 7/1974 | Suekane et al. | 435/94 |
| 4,025,389 | 5/1977 | Poulsen et al. | 435/94 |
| 4,275,156 | 6/1981 | Yoshioka et al. | 435/94 |
| 4,276,379 | 6/1981 | Heady | 435/94 |
| 4,284,722 | 8/1981 | Tamuri et al. | 435/94 |
| 4,308,349 | 12/1981 | Foley et al. | 435/94 |
| 4,310,628 | 1/1982 | Leiser | 435/94 |
| 4,348,480 | 9/1982 | Brownewell | 435/234 |

*Primary Examiner*—Lionel M. Shapiro
*Attorney, Agent, or Firm*—Richard Kornutik

[57] ABSTRACT

Glucose is enzymatically isomerized to fructose at a temperature of from about 90° C. to about 130° C. by contact with chemically stabilized glucose isomerase. Chemical stabilization includes intramolecular cross-linking with a cross-linking agent, and copolymerization into a polymer matrix wherein the isomerase is attached to the polymer matrix by covalent bonds and/or hydrogen and electrostatic bonds.

39 Claims, No Drawings

PROCESS FOR ISOMERIZING GLUCOSE

BACKGROUND OF THE INVENTION

This invention relates to enzymatic processes for converting glucose (dextrose) to fructose (levulose).

Most food grade glucose is provided as an enzymatic hydrolysate of corn starch, i.e., the corn syrup of commerce. Glucose is generally rated at being 60 to 80% as sweet as sucrose and therefore sells at a correspondingly lower price. It has long been known to isomerize glucose to fructose (which is even sweeter than sucrose) employing an enzyme having glucose isomerase activity, preferably one which has been immobilized upon an inert support such as diethylaminoethyl-cellulose, porous glass or chitin. Detailed descriptions of the enzymatic conversion of glucose to fructose employing glucose isomerase can be found in Hamilton, et al. "Glucose Isomerase a Case Study of Enzyme-Catalysed Process Technology", *Immobilized Enzymes in Food and Microbial Processes*, Olson et al., Plenum Press, New York, (1974), pp. 94-±06, 112, 115-137; Antrim, et al., "Glucose Isomerase Production of High-Fructose Syrups", *Applied Biochemistry and Bioengineering*, Vol. 2, Academic Press (1979); Chen, et al., "Glucose Isomerase (a Review)", *Process Biochem.*, (1980), pp. 30-35; Chen, et al. "Glucose Isomerase (a Review)", *Process Biochem.*, (1980), pp. 36-41; Nordahl, et al., "Fructose Manufacture from Glucose by Immobiled Glucose Isomerase", *Chem. Abstracts*, Vol. 82, (1975), Abs. No. 110316h; and Takasaki, "Fructose Production Glucose Isomerase", *Chem. Abstracts*, Vol. 82, (1975), Abs. No. 110316h; and Takasaki, "Fructose Production by Glucose Isomerase", *Chem. Abstracts*, Vol. 81, (1974), Abs. No. 76474a. In addition, there are numerous patents relating to glucose isomerization of which U.S. Pat. Nos. 3,616,221; Reissue No. 28,885 (originally U.S. Pat. No. 3,623,953); 3,694,313; 3,708,397; 3,715,276; 3,788,945; 3,826,714; 3,843,442; 3,909,354; 3,960,663; 4,144,127; and, 4,308,349 are representative.

The levels of fructose achievable by the isomerization of glucose with glucose isomerase is limited by the equilibrium of the isomerase reaction. At 65° C., the equilibrium of the reaction stands at approximately 51% fructose by weight from a starting substrate of pure dextrose. When refined glucose liquor is used as the substrate (containing up to about 6% nonmonosaccharides by weight) and allowing for a reasonable residence time in the enzyme reactor, an approximately 50% fructose syrup is the highest fructose content which can be obtained (on a dry basis) by the prior procedures referred to. To attain syrups of higher fructose content, fractionation systems must be employed which add greatly to the cost of the final product. At higher temperatures, however, the equilibrium becomes more favorable. For example, an enzymatic glucose isomerase process capable of being operated at temperatures of from about 90°-130° C. could be used to directly provide high fructose corn syrups (HFCS) containing 53-60 weight percent fructose on a dry basis thereby eliminating the need for fractionation and recycle. However, the tendency of known glucose isomerase systems to undergo thermal denaturation with an accompanying sharp reduction in activity has thus far frustrated attempts to utilize higher temperature regimes to force the equilibrium of the isomerization further in favor of fructose. Moreover, glucose and especially fructose are sensitive reducing sugars which have a marked tendency to form unwanted byproducts such as psicose, colored products, color precursors and acids when heated to the temperatures necessary to isomerize according to this invention. It has been speculated that the primary cause of thermal denaturation of proteins in general is the unfolding of the polypeptide chain and that such denaturation can be sharply retarded provided the protein globule is rigidified by attachment to a relatively rigid support in a multipoint fashion as described in Martinek, et al. Biochimica et Biophysica Acta, 485 (1977) 1-12, Elseview/North-Holland Biomedical Press. Torchilin, et al., Biochimica et Biophysica Acta, 522 (1978) 277-283, Elsevier/North-Holland Biomedical Press, reports a marked increase in the thermostability of alpha-chymotrypsin and succinylated alpha-chymotrypsin resulting from intramolecular crosslinkages achieved by activating the carboxylic acid groups of the enzyme with 1-ethyl-3-(3-dimethyl-aminopropyl)carbodiimide followed by treatment with a diamine such as tetramethylenediamine. The authors do not state to what extent, if any, enzyme activity is affected by such crosslinking.

It is known from Japanese Patent NS No. 48-1181 to treat microbial cells containing glucose isomerase with the dialdehyde, glutaraldehyde, to bridge, or crosslink, the enzyme molecules. According to U.S. Pat. No. 3,796,634, extracellular glucose isomerase is first adsorbed on colloidal particles and thereafter treated with glutaraldehyde. U.S. Pat. No. 4,144,127 describes an immobilization procedure in which glucose isomerase is adsorbed upon colloidal silica followed by addition thereto of a bifunctional agent such as glutaraldehyde. U.S. Pat. No. 3,669,841 describes a general procedure for immobilizing enzymes, e.g., an isomerase, wherein the enzyme is linked to a siliceous carrier employing a crosslinking agent such as a dialdehyde of 2 to 8 carbon atoms of which glyoxal, glutaraldehyde, malonic aldehyde and succinaldehyde are representative.

SUMMARY OF THE INVENTION

In accordance with the present invention, the thermostability of the glucose isomerase is significantly increased with the enzyme still retaining appreciable activity by reacting the isomerase with a crosslinking agent under conditions whereby appreciable crosslinking occurs and/or by incorporating the isomerase into a polymer matrix under conditions whereby multipoint attachment of the isomerase to the polymer occurs by means of covalent, hydrogen and/or electrostatic bonds. Enzyme so treated is termed "chemically stabilized enzyme" for the purpose of this disclose.

The thermostability of the glucose isomerase is significantly increased by the aforesaid chemical stabilization with the enzyme still retaining appreciable glucose isomerization activity. If desired, the chemically stabilized glucose isomerase can then be immobilized upon an inert support employing known and conventional techniques. Due to the enhanced thermostability of the chemically stabilized enzyme the enzyme can be employed in a high temperature glucose isomerization operation which would otherwise lead to significant enzyme inactivation if not stabilized.

In accordance with the present invention, glucose is isomerized to glucose-fructose syrup by the process which comprises contacting a glucose-containing liquor containing from about 20 to about 65 weight percent glucose with chemically stabilized glucose isomerase at a temperature of from about 90° C. to about 130° C. at a pH of from about 3 to about 8 and a contact time of from about 10 seconds to about 5 hours to convert at least about 53 to about 60 weight percent of the glucose present in said liquor to fructose with formation of less than 1% psicose and increase in color of less than 20 (CIRF×100).

The preparation of stabilized glucose isomerase is not dependent upon the use of a particular glucose isomerase but can be carried out with any glucose isomerase. It is, however, within the scope of the present invention to utilize a glucose isomerase particularly noted for its thermal stability, for example, glucose isomerase produced by *Bacillus stearothermophilus* as disclosed in U.S. Pat. No. 3,826,714 and glucose isomerase produced by microorganisms of the genus Ampullariella as disclosed in U.S. Pat. No. 4,308,349.

In addition, thermally stable glucose isomerase can be obtained using *Bacillus licheniformis* as described in European Patent Application No. 41,213 as well as using thermophiles of the genera Thermoactinomyces, Thermopolyspora, Thermomonospora, and Pseudonocardia as described in Japanese Patent Publication 74 305588 (C.A. 81; 76474a). Each of these references is incorporated herein by reference.

Several general methods for the chemical stabilization of enzymes are known all of which are believed to result in rigidification of the enzyme molecule to the extent that the unfolding of the enzyme molecule with consequent loss of active configuration that accompanies thermal denaturation is significantly hindered or prevented. Thus, chemical stabilization can be effected by internal rigidification whereby the enzyme molecule is crosslinked intramolecularly with various difunctional agents capable of establishing covalent bonds with the free amino and/or carboxylic groups of the enzyme. Examples of such stabilization are discussed by Torchilin, et al in Biochem. Biophys. Acta 522, 277–283 (1978), Martinek, et al. in J. Solid Phase Biochem. 2, 343–85 (1977) and Trochilin et al. in Biochem. Biophys. Acta 568, 1–10 (1979).

Chemical stabilization can also be effected by external rigidification whereby the enzyme molecule is attached in a multipoint fashion to a three dimensional polymer matrix formed around the molecule in such fashion that the matrix material is proximal to the surface of the active enzyme and is complementary to it. The bonds attaching the enzyme to the matrix may be covalent bonds as when the enzyme is first derivatized with a vinyl monomer and the enzyme so modified-copolymerized with various vinyl monomers as described by Martinek et al. in Biochem. Biophys. Acta 485, 1–12 (1977) and by Kulys et al. in Biokhimiya, 42, No. 3, 453–59 (1978).

Alternatively the bonds may be electrostatic or hydrogen bonds as when the enzyme is enmeshed within the confines of a concentrated three dimensional polymer network as discussed by Martinek et al. in Biochem. Biophys. Acta 485, 13–28 (1977) and by Kulys et al. in J. Solid Phase Biochem. 3, 95–105 (1978).

DESCRIPTION OF THE PREFERRED EMBODIMENT

The glucose which is isomerized to fructose in accordance with the present invention can be derived from any of the known sources for this sugar. For reasons of economy, the glucose will usually be derived from the hydrolysis of cellulose or starch employing acid and/or enzyme, preferably the latter, in accordance with known procedures. Glucose containing liquors obtained in this way will typically contain minor quantities of polysaccharides, sugar oligomers, etc., depending upon the carbohydrate source employed and the hydrolysis method utilized. Cereal grains such as corn, milo, wheat, rye, and the like, and amylaceous roots and tubers such as potatoes, yams, carrots, cassava (manioc), and the like, are excellent sources of starch for conversion to the glucose starting material of this invention. In the United States, corn starch is especially preferred due to its comparatively low cost and ready availability. Since the production of food grade glucose favors the use of enzymatic starch hydrolysis procedures, such procedures are preferred herein. Enzyme hydrolysis methods are described in U.S. Pat. Nos. 4,017,363, 3,912,590, 3,922,196, 3,922,197–201 and 4,284,722, the disclosures of which are incorporated by reference herein.

The glucose isomerase employed herein as the source of enzyme for chemical stabilization can be isolated from among any of the known glucose isomerase-producing microorganisms including *Streptomyces flavorirens, Streptomyces achromogenes, Streptomyces echinatus, Streptomyces albus, Streptomyces wedmorensis, Streptomyces phaeochromogenes, Streptomyces bobiliae, Streptomyces olivochromogenes, Streptomyces venezuelae, Aerobacter aerogenes, Aerobacter cloacae, Bacillus coagulans, Bacillus megaterium, Bacillus fructosus, Brevibacterium pentaaminoacidicum, Escherichia intermedia, Leuconostoc mesenteroides,* and *Paracolobactrum aerogenoides.* In addition, glucose isomerases elaborated by the genus Nocardia, Micromonospora, Microbispora, Microellobospora and Arthrobacter can be used. Streptomyces sp. ATCC 21,175 is an excellent source for glucose isomerase for use in the process of this invention. As previously stated, it can be advantageous to utilize glucose isomerase which possesses stability at the relatively high isomerization temperatures employed herein, e.g., glucose isomerase produced by *Bacillus stearothermophilus,* in particular, strains selected from the group consisting of *Bacillus stearothermophilus* ATCC 21,365, NRRL B-3680, NRRL B-3681 and NRRL B-3682 as disclosed in U.S. Pat. No. 3,826,714; glucose isomerase produced by a microorganism of the genus Ampullariella such as *Ampullariella digitata, Ampullariella lobata, Ampullariella campanulata* and *Ampullariella regularis* (U.S. Pat. No. 3,826,714); glucose isomerase produced by *Bacillus licheniformis* (European Patent Application No. 41213); and glucose isomerase produced by the thermophiles of the genera described in Japanese Patent Publication 74 30588.

In addition to the aforementioned microorganisms, the present invention contemplates the use of mutants and variants thereof as well as genetically transformed microorganisms derived therefrom by introduction of mutated glucose isomerase genes into other microorganisms, including mesophilic and preferably thermophilic microorganisms. The mutated glucose isomerase genes selected for such use are those which provide glucose isomerase which is stable at elevated temperatures, especially above 90° C. and preferably up to about 130° C. Such genes can be prepared by the usual techniques used for mutation of microorganisms such as irradiation or chemical means. Thus, isolated glucose isomerase genes which produce glucose isomerase of moderate thermal stability, as produced for example by certain Streptomyces strains, on in vitro mutagenesis will undergo mutation, and selection of the appropriate mutated genes is accomplished by reintroduction of the mutated gene into either the parent or other organism, preferably a thermophilic organism, followed by replication of the organism and testing of the thermal stability of the resulting glucose isomerase.

Since glucose isomerase is produced intracellularly by these and other microorganisms, a source of glucose isomerase can be provided by simply harvesting the cells, and the enzyme can be separated from the cells by techniques known in the art, e.g., cell autolysis, sonic disruption, and employed in an enzyme reactor of known and conventional design. Preferably, the chemically stabilized glucose isomerase can be immobilized on an inert substrate in accordance with known and conventional procedures if it is not insolubilized as a consequence of chemical stabilization. Materials and procedures used for the immobilization of enzymes are well known and are described in a number of publications including Wang, et al., Fermentation & Enzyme Technology, John Wiley & Sons, Inc., New York (1979), pp. 318-338 and Kirk-Othmer, Encyclopedia of Chemical Technology, 3rd Ed., John Wiley & Sons, Inc., New York (1980) Vol. 9 pp. 148-172, the disclosures of which are incorporated by reference herein. The presence of small quantities of cobalt, manganese and magnesium cation and/or water soluble salt of sulfurous acid such as sodium sulfite, sodium bisulfite, magnesium sulfite, and/or magnesium bisulfite as taught in U.S. Reissue Pat. No. 28,885 to reduce or inhibit denaturation of the glucose isomerase during operation of the process is also contemplated.

It is necessary that the concentration of glucose in the glucose-containing feed liquor be within the range of from about 20 to about 65, and preferably from about 30 to about 50, weight percent if the desired results are to be achieved.

It is also necessary that the isomerization be carried out at a pH within the range of from about 3.0 to about 8.0 more preferably within the range of from about 4.0 to about 7.0 and most preferably between 5.0 and 6.5. Operation of the isomerization significantly below or above the aforestated pH range will lead to the formation of excessive quantities of undesirable by-products such as psicose, organic acids, colored products, color precursors, fructose dianhydrides and the like.

Yet another necessary requirement of the present invention lies in the duration of contact of the glucose-containing feed liquor and the chemically stabilized glucose isomerase. Such contact must be maintained within the range of from about 10 seconds to about 5 hours, preferably from about 30 seconds to about one hour and most preferably from about two minutes to about 30 minutes to provide fructose syrup of acceptable quality.

The preferred contact time between the chemically stabilized glucose isomerase and the glucose containing liquor depends to a large extent upon the pH at which the isomerization reaction is conducted. At the lower end of the pH range, longer contact time can be tolerated without causing undue degradation of glucose and fructose through formation of psicose and other undesirable degradation products. At the upper end of the range, shorter contact time is necessary to avoid psicose and color formation. In practice, the total time the glucose containing syrup is at or near the final reaction temperature is reckoned as the effective contact time since the sugar degradation reactions which occur are nonenzymatic and take place whether or not the liquor is in contact with the glucose isomerase. Therefore, in conducting isomerizations above 90° C. it is important to minimize the time required to bring the glucose liquor to the desired isomerization temperature (as for example, by mixing the liquor with steam just before or during contact with the isomerase) and once the desired fructose level has been achieved to thereafter rapidly separate the liquor from any active isomerase and then cool the liquor as quickly as possible to less than 90° C. and preferably to less than 70° C. If a soluble form of chemically stabilized glucose isomerase is used it will be necessary to inactivate such (as for example, by pH reduction to a range that will inactivate the isomerase) before the cooling step to avoid any reconversion to glucose of the fructose formed during the high temperature isomerization step since the isomerization reaction is, of course, reversible.

The maximum degree of conversion of glucose to fructose that can be attained is governed by the thermodynamic equilibrium between glucose and fructose which in turn is dependent upon the temperature at which the isomerization is conducted. Very careful analysis of equilibrium mixtures of glucose and fructose has established the following relationship.

$$F = 41.5 + 0.157T \quad (1)$$

where F is the % fructose at equilibrium based on total weight of glucose and fructose and T is the temperature (°C.) at which isomerization is conducted.

Contact time between the glucose containing syrup and isomerase in a reactor can generally be reckoned by reference to the following formula when a reactor containing an immobilized form of isomerase is used.

$$t = \frac{CV \ln \frac{F_e - F_o}{F_e - F}}{kA} \quad (2)$$

where
 $t$ = the contact time
 $C$ = concentration of glucose and fructose
 $V$ = The free volume of fluid in the packed bed (volume of bed minus the volume occupied by the immobilized enzyme particles)
 $F_e$ = fraction of fructose in the glucose/fructose mixture at equilibrium when at the isomerization temperature
 $F_o$ = fraction of fructose (based on G+F) at the entrance to the packed bed
 $F$ = fraction of fructose (based on G+F) in the solution exiting the packed bed
 $k$ = reaction rate constant for isomerization at the isomerization conditions
 $C$ = concentration of glucose and fructose in solution
 $A$ = activity of isomerase in the packed bed Values of k for immobilized isomerase prepared according to the examples following range from about 0.15 to about 5 g hr$^{-1}$ IGIU$^{-1}$ at temperatures from 90° C. to 130° C. respectively. This relationship shows the need to minimize contact time at high temperature by using packed beds of high activity per unit volume. Packed beds formed according to the procedures in the following examples can contain up to 2000 IGIU/ml which can result in attainment of 99.5% of equilibrium fructose content in a high temperature reactor in less than one minute when staged reactors are used at different temperatures and the feed to a first reactor is isomerized at low temperature before isomerizing at high temperature in a second reactor. Therefore, use of high potency packed beds can lead to very low effective contact times which in turn minimizes the degradation of fructose which occurs at the high temperatures required for this invention.

In commercial practice, however, fructose containing syrups are not manufactured from pure glucose. Rather, starch hydrolysates (as prepared in the above mentioned references) are used as the glucose source and these invariably contain non-glucose and non-fructose saccharides (hereinafter referred to as polysaccharides) derived from incomplete hydrolysis of starch, and the reversion of glucose. Typically these constitute from 3% to 8% of the total dry weight as the saccharides derived by starch hydrolysis. It is therefore necessary when reckoning the temperature at which isomerization is to be conducted to allow for any polysaccharide contained in the glucose liquor as well as other factors such as the total dry basis fructose content to be attained, formation of psicose and other nonglucose and nonfructose products during the effective contact time of the glucose liquor and the isomerase. Relationships for the calculation of isomerization temperature are shown below:

$$T = \frac{E - 41.5}{0.157} \quad (3)$$

$$E = \frac{10,000 (M + C)}{Q(100 - P)} \quad (4)$$

T = isomerization temperature (°C.)
E = equilibrium fructose content (% based on total glucose + fructose) at temperature T.
M = % fructose dry basis required in the isomerized product.
C = % psicose + other degradation products formed during the effective isomerization contact time.
Q = % of equilibrium attained during isomerization reaction.
P = % polysaccharide content of glucose liquor.

Typically, less than 1% and preferably less than 0.5% psicose and other degradation products will be formed and 99.5% of equilibrium can be attained. Therefore, to prepare syrups with 55.5% fructose (dry basis), the following isomerization temperatures are required for glucose liquors of the indicated polysaccharide contents.

| Polysaccharide in Glucose liquor (% dry basis) | Isomerization Temperature (°C.) |
| --- | --- |
| 0 | 94.7 |
| 1 | 98.3 |
| 2 | 102.0 |
| 3 | 105.8 |
| 4 | 109.7 |
| 6 | 117.6 |
| 8 | 126.0 |

The accepted article of commerce contains on the average, 55.5% fructose on a dry basis. This is so because at this fructose level, high fructose corn syrup (HFCS) attains equal sweetness with sucrose on a weight for weight dry basis. Moreover, HFCS of 55.5% fructose content is firmly established as the article of commerce that is used interchangably as a total or partial replacement for sucrose in many food products and especially in carbonated soft drinks. Consumption of this type of HFCS in the U.S. is expected to be 2.9 billion pounds in 1982 with growth to 4.0 billion pounds in 1983. Owing to the complexities inherent in delivering, storing, metering and formulating HFCS into food products, there is a universal demand for uniformity of product from one HFCS manufacturer to another so that product from different supply sources can be used intechangably and simultaneously. Therefore, fructose level of 55–56% dry basis has attained special significance as a target level in the technology associated with HFCS manufacture.

The present process provides fructose levels of at least 53%, preferably at least 54% and most preferably at least 55%.

With the foregoing requirements of glucose concentration, pH and contact time in mind, known glucose isomerization processes can be suitably adapted to operate at from about 90° to about 130° C. to provide the high glucose-fructose syrups of this invention.

Chemical stabilization of isomerase is effected by a number of different methods which can result in increased thermal stability. The fundamental approach is to introduce structural elements into the enzyme molecule in such a manner that the enzyme will resist unfolding when heated beyond its normal thermal denaturation point. The preferred method for accomplishing this is to modify the enzyme by chemical substitution thereon of moieties containing polymerizable vinyl groups such that the latter are firmly attached to the surface of the enzyme molecule at several points. Thereafter, the modified enzyme is mixed with one or more polymerizable vinyl compounds in aqueous solution and the mixture copolymerized to form the chemically stabilized enzyme wherein the enzyme is firmly bonded at numerous points to a three dimensional polymeric matrix which has formed a structure complemtary in shape to that of the enzyme.

It is essential when conducting the above reactions that conditions that can lead to denaturation of the isomerase with consequent loss of activity be avoided. For example, extremes of pH and temperature must be avoided during any and all of the manipulations necessary to carry out the above reactions.

Examples of reagents that are used to modify isomerase to substitute polymerizable vinyl groups thereon are acryloyl chloride, methacryloyl chloride, acrolein, crotonaldehyde, maleic anhydride, 3,4-epoxybutene, acrylic acid-2,3-epoxypropyl ester, acrylic acid-2,3-thioglycidyl ester, 1-allyloxy-3-(N-ethyleneimine)-2-propanol, acrylic acid-O-succinamide ester, chloromaleic acid anhydride, maleic acid azide, 3-bromopropene, and allyl isothiocyanate. Such compounds are capable of reacting with the free amino groups of isomerase, for example, the -amino group of lysine moieties.

Still other compounds capable of reacting with the free carboxylic acid groups of isomerase may be employed to substitute readily polymerizable vinyl moieties thereon as will be apparent to the skilled artisan.

Examples of vinyl compounds that can be copolymerized with the modified isomerase are sodium acrylate, sodium methacrylate, acrylamide, hydroxyethyl methacrylate, ethyleneglycol methacrylate, acryloyl-piperdine-4-sprio-2'-(1',3'-dioxacrylopentane), 1-acryloyl-4-piperidone, and acryloylmethoxyamine. Generally, water soluble monomers or monomer mixtures that will result in water soluble polymers (if polymerized in the absence of crosslinking agents) are preferred.

Typically, difunctional vinyl compounds are included in the monomer mixture (0.1-5% of the total monomer) to provide crosslinking sites which lead to a three dimensional polymer network. Suitable compounds are N,N'-methylene-bisacrylamide and ethylene glycol dimethacrylate. When these are used, the polymerized mixture forms an insoluble gel which results in immobilization of the isomerase.

Initiation systems commonly used in vinyl polyermizations are suitable such as ammonium persulfate plus sodium bisulfite, hydrogen peroxide plus ferrous sulfate, potassium sulfate plus N,N,N',N'-tetramethylethylenediamine, and riboflavin (plus light).

Alternatively, noncovalent bonding to the three dimensional polymer matrix may be sufficient to confer the desired rigidity to the isomerase molecule and thereby effect a significant increase in thermostability. This can occur when isomerase is mechanically entrapped within a crosslinked polymeric gel. In this case, it is not necessary that the isomerase be modified by attachment of a vinyl compound thereto prior to the polymerization step. However, concentration of the gel must be greater than about 30% by weight before significant stabilization occurs and gels of about 50% concentration are preferred. Monomers capable of giving polymer gels that can form electrostatic and hydrogen bonds with the isomerase are required as, for example, sodium acrylate, sodium methacrylate, acrylamide, and hydroxyethylmethacrylate.

A third method of isomerase rigidification is intramolecular crosslinking which is capable of conferring added thermostability.

Suitable crosslinking agents for use in the present invention include difunctional compounds which are capable of reacting with pendant functional groups on the enzyme molecule. Most commonly, such functional groups are amino groups, generally primary amino groups which can react with a wide variety of functional groups such as carboxylic acid, sulfonyl halide, aldehydes, isocyanates, propiolates, and the like.

Thus, the crosslinking agents include dicarboxylic acid anhydrides such as succinic anhydride and adipic anhydride; the corresponding dialdehydes such as glyoxal, succinaldehyde and glutaraldehyde; unsaturated compounds such as acrolein and crotonaldehyde, diol propiolates such as ethylene glycol bispropiolate, propylene glycol bispropiolate and hexamethylene glycol bispropiolate; and disulfonyl halides such as benzene-1,3-disulfonyl chloride; naphthalene-1,5-disulfonyl chloride and tolyl-2,4-disulfonyl chloride.

In addition, since the enzyme contains or can be made to contain acid groups reactive with amines, then difunctional amines can be used as crosslinking agents for the present invention. These include, for example, diamines containing up to 8 carbon atoms e.g, phenylenediamine, butylenediamine, hexylenediamine, octylenediamine, pentylenediamine, ethylenediamine and dodecylenediamine.

The amount of crosslinking agent can vary considerably, the ratio of enzyme to crosslinking agent ranging from about 0.1 to about 0.0001. The method of effecting the requisite bonding will be determined to a certain degree by the nature of the selected crosslinking agent and the enzyme. In general, the reagents will be dissolved in a suitable inert solvent medium and the reaction should proceed at reasonably low temperatures to avoid adverse affects on the enzyme which can be sensitive to high temperatures. Usually, reactions at or near room temperature are preferred and water or aqueous solvents are used as reaction medium.

Activity of the soluble isomerase preparation was determined as described by Lloyd et al. in Cereal Chemistry, 49, No. 5, pp. 544-553 (1972). One IGIU is the amount of isomerase that converts 1 micromole of glucose to fructose per minute in a solution containing 2 moles of glucose per liter, 0.02 moles of $MgSO_4$ per liter, and 0.001 moles of $CoCl_2$ per liter at a pH of 6.85 (0.2 M sodium maleate) and a temperature of 60° C. when determined by the above method.

The following example is further illustrative of the process of this invention.

EXAMPLE

This example shows direct isomerization of a glucose containing liquor to attain a composition with greater than 55% fructose on a dry basis wherein a two stage isomerization process is used. A first low temperature isomerization is conducted at 70° C. and the product of that reaction is used as feed to a second high temperature reactor (110° C.) containing a chemically stabilized isomerase wherein the fructose content is increased to greater than 55% dry basis.

PREPARATION OF STABILIZED ISOMERASE

A soluble glucose isomerase was prepared by a method similar to that described in U.S. Pat. No. 3,788,945.

A species of Streptomyces rubigenosus derived from S. rubigenosus ATCC 21175 is grown by submerged aerobic fermentation on a medium with the following composition:

|  | % by Weight |
| --- | --- |
| Dextrose | 9.0 |
| Corn steep Liquor (Solids) | 1.6 |
| Diammonium Phosphate | 0.08 |
| Manganese Sulfate | 0.06 |
| Antifoam (Pluronic PL-61) | 0.003 |

The medium is sterilized at 121° C. for 45 min., cooled and adjusted to pH 6.8-7.0. It is inoculated with 14% (v/v) of an inocula comprising the contents of a seed fermenter prepared with the S. rubigenosus variant mentioned above. Fermentation is conducted under aseptic conditions at 30° C. for about 60 hours with aeration at 0.65 vvm. S. rubigenosus ATCC 21175 can also be used for inoculation and production of isomerase in which case media of the following composition is used.

|  | % by Weight |
| --- | --- |
| Dextrose | 0.24 |
| Corn Steep Liquor (solids) | 1.5 |
| Sorbitol | 1.6 |
| Cobatous chloride | 0.02 |
| Diammonium Phosphate | 0.56 |
| Xylose | 1.0 |

Glucose isomerase is extracted from the S. rubigenosus by adding 0.35% Maquat MC 1412 (Mason Chemical Co.), and 10 ppm of hen's egg lysozyme and agitating for 5 hrs. at 40° C., pH 6.3-6.6. The mixture is then filtered to provide a solution of crude, unpurified glucose isomerase.

The crude isomerase is purified by adsorption on DEAE-cellulose (made according to U.S. Pat. No. 3,823,133), filtering and washing the adsorbed product with 0.1 M NaCl solution to remove impurities and then desorbing the isomerase by contacting with 0.45 M NaCl solution. The pH of all solutions is maintained at 7.5 during the purification steps. The solution of partially purified isomerase obtained thereby is mixed with 3 volumes of 95% ethanol at 0° C. to precipitate the isomerase. Perlite filter aid is added, the solids recovered by filtration and air dried to provide a soluble isomerase preparation containing 2500 IGIU/g. Specific activity of the isomerase preparation is about 40 IGIU/mg of protein.

The purified isomerase is dissolved in water to provide a solution containing 1 mg isomerase per ml at room temperature and the mixture filtered to remove filter aid. The resulting solution is concentrated by ultrafiltration using a membrane with a 50,000 molecular weight cutoff to provide a solution with 20 mg enzyme/ml and is then diafiltered in the ultrafiltration apparatus with 4 volumes of water to remove low molecular weight substances.

The resulting isomerase concentrate is stabilized according to the procedure outlined by Martinek et al. (Biochem Biophys. Acta, 485, 1-12 (1977).

Fifty ml of 2 M sodium phosphate buffer (pH 8) is mixed with 500 ml of isomerase concentrate and cooled to 0° C. Cobalt chloride is dissolved therein to provide 1 mM cobalt ion. Five g of acryloyl chloride is added in small portions with rapid stirring over a period of 30 minutes while maintaining pH at 8.0 with concentrated potassium hydroxide solution. The solution is stirred gently at 0° C. for another 30 minutes. The solution containing the acryloylated isomerase is diafiltered with two volumes of 0.1 M phosphate buffer at pH 8.0 and is then concentrated to 50 mg protein/ml by ultrafiltration. One hundred ml of the concentrate is mixed with 30 g of acrylamide, 2 g of N,N'-methylene-bis-acrylamide, and 3.0 mg riboflavin and the resulting solution placed in a shallow layer (0.5 cm) in a glass vessel cooled in an ice bath. The solution is illuminated with a 300 watt lamp until polymerization is complete (about 2 hours). The resulting gel is removed from the dish, cut into 0.5 inch pieces, further comminuted and then sieved to give a fraction which is 30–60 mesh. The resulting product is washed thoroughly with distilled water to provide a chemically stabilized glucose isomerase preparation in immobilized form.

PREPARATION OF ISOMERASE REACTORS

A low temperature (70° C.) isomerase reactor is constructed by packing isomerase immobilized on DEAE-cellulose (prepared according to U.S. Pat. No. 3,788,945) into a 1" diameter glass column equipped with inlet and outlet and with a jacket for the circulation of water from a thermostat. The headspace over the packing contains a thermometer and is otherwise filled with glass beads to minimize dead space as far as practical. The reactor contains enough immobilized isomerase to provide 20,000 IGIU and the packed bed is about 15 cm high.

A high temperature reactor is similarly constructed but is fitted with a backpressure valve at the outlet to enable the internal pressure of the system to be maintained at a level high enough to avoid boiling of the liquid therein at the intended isomerization temperature. Chemically stabilized isomerase prepared as above is packed into the reactor to provide a bed having 2000 IGIU.

PREPARATION OF GLUCOSE CONTAINING SOLUTION

A starch hydrolysate is prepared according to known methods wherein corn starch is liquefied (for example as described in U.S. Pat. No. 3,644,126, Example 1) and subsequently saccharified (for example, according to U.S. Pat. No. 3,280,006, Example 1). The saccharified starch liquor obtained thereby is refined according to U.S. Pat. No. 3,834,940 to yield a glucose containing syrup. A glucose containing solution is prepared from this with the following composition.

| | |
|---|---|
| Total Dry Substance (%) | 50 |
| Glucose (% Dry Basis) | 97.0 |
| Polysaccharide (% Dry Basis) | 3.0 |
| Psicose (% Dry Basis) | nil |
| $NaHSO_3$ (mM) | 5 |
| $MgSO_4$ (mM) | 2 |
| $CoCl_2$ (mM) | 0.1 |
| pH | 6.5 |

TWO STAGE ISOMERIZATION

The glucose containing solution described above is pumped through the first low temperature reactor at 5 ml/min while maintaining the reactor temperature at 70° C. The effluent from the low temperature isomerization is then pumped through the high temperature reactor at 5 ml/min. while maintaining pressure in the reactor at a value of at least 50 psi. Effluent from the high temperature reactor is immediately cooled to less than 50° C. and is pH adjusted to pH 5.0 with HCl. Analysis of the glucose containing solution used as feed to the reactors and of the effluents from the low and high temperature reactors typically gives results as shown in Table 1.

Carbohydrate content is determined by method E-61 and color by method F-14 of the Standard Analytical Methods of the Member Companies and the Corn Refiners Association, Corn Refiners Association, Inc.; 1001 Connecticut Avenue, Washington, D.C. 20036. The color values obtained by method F-14 are multiplied by 100 and are reported as (CIRF×100).

The results shown in Table 1 are typical of the process of this invention which is capable of producing compositions by direct isomerization with greater than 55% fructose while maintaining psicose at 1.0% dry basis or less and color production at less than 20 (CIRF×100).

TABLE 1

| Solution Treatment | Carbohydrate Composition (% by weight on an ash free dry basis) | | | | Color (CIRF × 100) |
|---|---|---|---|---|---|
| | Fructose | Glucose | Psicose | Poly-saccharide | |
| Unisomerized | 0 | 97.0 | 0 | 3.0 | 1.0 |
| Isomerized at 70° C. | 50.0 | 47.0 | 0.1 | 3.0 | 3.0 |
| Isomerized at 110° C. | 56.0 | 40.7 | 0.3 | 3.0 | 20 |

I claim:

1. A process for isomerizing glucose to fructose which comprises contacting a glucose-containing feed liquor containing from about 20 to about 65 weight percent glucose with chemically stabilized glucose

34. The process of claim 32 wherein the pH of the medium is maintained at about 5 to about 6.5.

35. The process of claim 32 wherein the contact time is from 2 minutes to 30 minutes.

36. A process for enzymatically converting glucose to fructose which comprises contacting a glucose-containing feed liquor containing from abut 20 to about 65 weight percent glucose with glucose isomerase at a temperature of from about 20° C. to about 80° C. at a pH of about 6.0 to 8.0 and a contact time of about one to about 2 hours to convert from 40 to about 50 weight percent of the glucose present in said liquor to fructose, increasing the temperature of the isomerization medium to from about 90° C. to about 130° C., adjusting the pH of the isomerization medium as necessary to within the range of from about 3 to about 8, contacting the fructose-containing liquor with the chemically stabilized glucose isomerase for an additional period of from about 10 seconds to about 5 hours to increase the conversion level to from about 53 to about 60 weight percent of the glucose present in the original glucose-containing feed liquor and thereafter cooling the product fructose-glucose syrup to a temperature of from about 20° C. to about 80° C., there being no substantial formation of psicose and thereafter cooling the reaction mixture to a temperature below 80° C. after the enzyme has been removed from contact with the reaction mixture.

37. The process of claim 36 wherein the glucose containing feed liquor is contacted with chemically stabilized glucose isomerase at a temperature of from about 95° C. to about 115° C.

38. The process of claim 36 wherein the pH of the medium is maintained at about 5 to about 6.5.

39. The process of claim 36 wherein the contact time is from 2 minutes to 30 minutes.

* * * * * isomerase at a temperature of from about 90° C. to about 130° C. at a pH of from about 3.5 to about 8 and a contact time of from about 10 seconds to about 5 hours to convert at least about 53 to about 60 weight percent of the glucose present in said liquor to fructose with no substantial formation of psicose.

2. The process of claim 1 wherein the glucose-containing liquor is obtained from the hydrolysis of corn starch.

3. The process of claim 1 wherein the source of the glucose isomerase is a microorganism selected from the group consisting of Streptomyces species, mutants, variants and genetic modifications thereof.

4. The process of claim 1 wherein the source of the glucose isomerase is a microorganism selected from the group consisting of Streptomyces sp. ATCC 21175; mutants, variants, and genetic modifications thereof.

5. The process of claim 1 wherein the source of the glucose isomerase is a microorganism into which a mutated glucose isomerase gene has been introduced said mutated gene providing glucose isomerase of high thermal stability.

6. The process of claim 1 wherein the glucose isomerase is a thermally stable glucose isomerase.

7. The process of claim 6 wherein the thermally stable glucose isomerase is obtained from Bacillus Stearothermophilus.

8. The process of claim 6 wherein the thermally stable glucose isomerase is obtained from *Bacillus licheniformis*.

9. The process of claim 6 wherein the thermally stable glucose isomerase is obtained from a thermophile of the genera Thermoactinomyces, Thermopolyspora, Thermomonospora or Pseudonocardia.

10. The process of claim 6 wherein the thermal stable glucose isomerase is obtained from a microorganism of the genus Ampullariella.

11. The process of claim 1 wherein an enzyme denaturation-inhibiting amount of water soluble salt of sulfurous acid is present in the isomerization medium.

12. The process of claim 1 wherein the glucose-containing feed liquor contains from about 30 to about 50 weight percent glucose.

13. The process of claim 1 wherein the glucose-containing feed liquor is contacted with chemically stabilized glucose isomerase at about 95° C. to about 115° C.

14. The process of claim 1 wherein the pH of the isomerization medium is maintained at about 5 to about 6.5.

15. The process of claim 1 wherein the contact time is from about 2 minutes to about 30 minutes.

16. The process of claim 1 wherein the chemically stabilized glucose isomerase is used in the immobilized form.

17. The process of claim 14 wherein the chemically stabilized glucose isomerase is immobilized upon diethylaminoethyl cellulose.

18. A process for enzymatically converting glucose to fructose which comprises contacting a glucose-containing feed liquor containing from abut 20 to about 65 weight percent glucose with glucose isomerase at a temperature of from about 20° C. to about 80° C. at a pH of about 6.0 to 9.0 and a contact time of about one to about 2 hours to convert from 40 to about 50 weight percent of the glucose present in said liquor to fructose, increasing the temperature of the isomerization medium to from about 90° C. to about 130° C., adjusting the pH of the isomerization medium as necessary to within the range of from about 3 to about 8, contacting the fructose-containing liquor with the chemically stabilized glucose isomerase for an additional period of from about 10 seconds to about 5 hours to increase the conversion level to from about 53 to about 60 weight percent of the glucose present in the original glucose-containing feed liquor and thereafter cooling the product fructose-glucose syrup to a temperature of from about 20° C. to about 80° C., there being no substantial formation of psicose.

19. The process of claim 18 wherein the glucose-containing liquor is obtained from the hydrolysis of corn starch.

20. The process of claim 18 wherein the source of the glucose isomerase is Streptomyces sp. ATCC 21175 or mutants, variants or derivatives thereof.

21. The process of claim 18 wherein the source of the glucose isomerase is a thermally stable glucose isomerase.

22. The process of claim 21 wherein the thermally stable glucose isomerase is obtained from *Bacillus stearothermophilus*.

23. The process of claim 21 wherein the thermally stable glucose isomerase is obtained from *Bacillus licheniformis*.

24. The process of claim 21 wherein the thermally stable glucose isomerase is obtained from a thermophile of the genera Thermoactinomyces, Thermopolyspora, Thermomonospora or Pseudonocardia.

25. The process of claim 21 wherein the thermally stable glucose isomerase is obtained from a microorganism of the genus Ampullariella.

26. The process of claim 18 wherein an enzyme denaturation-inhibiting amount of water soluble salt of sulfurous acid is present in the isomerization medium.

27. The process of claim 18 wherein the glucose-containing feed liquor contains from about 30 to about 50 weight percent glucose.

28. The process of claim 18 wherein the fructose-containing liquor resulting from the initial contacting step is further contacted with chemically stabilized glucose isomerase at about 95° C. to about 115° C.

29. The process of claim 18 wherein the pH of the isomerization medium following the initial contact step is adjusted to and maintained at about 5.5 to about 6.0.

30. The process of claim 18 wherein the chemically stabilized glucose isomerase is used in the immobilized form.

31. The process of claim 30 wherein the chemically stabilized glucose isomerase is immobilized upon diethylaminoethyl cellulose.

32. A process for isomerizing glucose to fructose which comprises contacting a glucose-containing feed liquor containing from about 20 to about 65 weight percent glucose with chemically stabilized glucose isomerase at a temperature of from about 90° C. to about 130° C. at a pH of from about 3.5 to about 8 and a contact time of from about 10 seconds to about 5 hours to convert at least about 53 to about 60 weight percent of the glucose present in said liquor to fructose with no substantial formation of psicose and thereafter cooling the reaction mixture to a temperature below 80° C. after the enzyme has been removed from contact with the reaction mixture.

33. The process of claim 32 wherein the glucose containing feed liquor is contacted with chemically stabilized glucose isomerase at a temperature of from about 95° C. to about 115° C.